US012690748B2

(12) United States Patent
Kim et al.

(10) Patent No.: US 12,690,748 B2
(45) Date of Patent: Jul. 28, 2026

(54) METHOD, PROGRAM, AND APPARATUS FOR CONTROLLING ENDOSCOPE DEVICE

(71) Applicant: MedInTech Inc., Seoul (KR)

(72) Inventors: Geono Kim, Seoul (KR); Chiwon Lee, Namyangju (KR); Myungjoon Kim, Gwacheon (KR)

(73) Assignee: MedIn Tech Inc., Seoul (KR)

( * ) Notice: Subject to any disclaimer, the term of this patent is extended or adjusted under 35 U.S.C. 154(b) by 0 days.

(21) Appl. No.: 18/969,197

(22) Filed: Dec. 4, 2024

(65) Prior Publication Data

US 2025/0185880 A1     Jun. 12, 2025

(30) Foreign Application Priority Data

Dec. 8, 2023    (KR) ........................ 10-2023-0177321

(51) Int. Cl.
*A61B 1/00*        (2006.01)

(52) U.S. Cl.
CPC ........ *A61B 1/00006* (2013.01); *A61B 1/0016* (2013.01)

(58) Field of Classification Search
CPC . A61B 1/00006; A61B 1/0016; A61B 1/0004; A61B 1/005; A61B 1/0051; A61B 1/008; A61B 1/009; A61B 1/01
See application file for complete search history.

(56) References Cited

U.S. PATENT DOCUMENTS

2011/0015786 A1*   1/2011   Kawai .................. A61B 1/0016
                                                   700/256
2014/0058406 A1     2/2014   Tsekos 2015/0054445 A1     2/2015   Kawai
2016/0228203 A1*   8/2016   Yamanaka ............. A61B 90/13
2017/0000574 A1*   1/2017   Itkowitz ............... A61B 1/0016
2019/0083190 A1*   3/2019   Graves .................... H04L 47/10
2020/0297442 A1*   9/2020   Adebar .................. A61B 34/30
2023/0301488 A1*   9/2023   Aklivanh ........... H04L 25/0272
2024/0324870 A1*   10/2024   Wong ..................... A61B 1/307
2024/0358444 A1*   10/2024   Zhao ...................... A61B 5/062

(Continued)

FOREIGN PATENT DOCUMENTS

JP      2009-131406 A     6/2009
JP      2009136618       6/2009
JP      2013-248119 A    12/2013

(Continued)

OTHER PUBLICATIONS

A Novel Position Compensation Scheme for Cable-Pulley Mechanisms Used in Laparoscopic Surgical Robots.

(Continued)

*Primary Examiner* — Michael J Carey
*Assistant Examiner* — William B Chou
(74) *Attorney, Agent, or Firm* — Harvest IP Law, LLP

(57) ABSTRACT

According to one embodiment of the present disclosure, there is disclosed a method of controlling an endoscope scope, which is performed by a computing device including at least one processor. The method includes: obtaining first data regarding the actual movement state of a motor included in an endoscope device and second data regarding the target movement state of a scope included in the endoscope device; and controlling the motor based on the obtained first data and second data.

13 Claims, 8 Drawing Sheets

(56) References Cited

U.S. PATENT DOCUMENTS

| 2025/0049293 | A1* | 2/2025 | Shelton, IV | ........... | A61B 1/046 |
| 2025/0108189 | A1* | 4/2025 | Blanco | ................... | A61B 34/71 |

FOREIGN PATENT DOCUMENTS

| JP | 7208752 | B2 | 1/2023 |
| JP | 2023-028474 | A | 3/2023 |
| KR | 10-1940046 | B1 | 1/2019 |
| KR | 10-2146307 | B1 | 8/2020 |
| KR | 10-2188195 | B1 | 12/2020 |
| KR | 10-2312584 | B1 | 10/2021 |
| WO | 2 151 184 | A1 | 2/2010 |
| WO | 2011058893 | | 5/2011 |

OTHER PUBLICATIONS

Office Action From Japanese Patent Office Dated Aug. 19, 2025.
Office Action From Japanese Patent Office Dated Jan. 20, 2026
Issued for Corresponding Japanese Patent Application.
Office Action From European Patent Office Dated Mar. 27, 2026
Issued for Corresponding European Patent Application.

* cited by examiner

Figure 4:
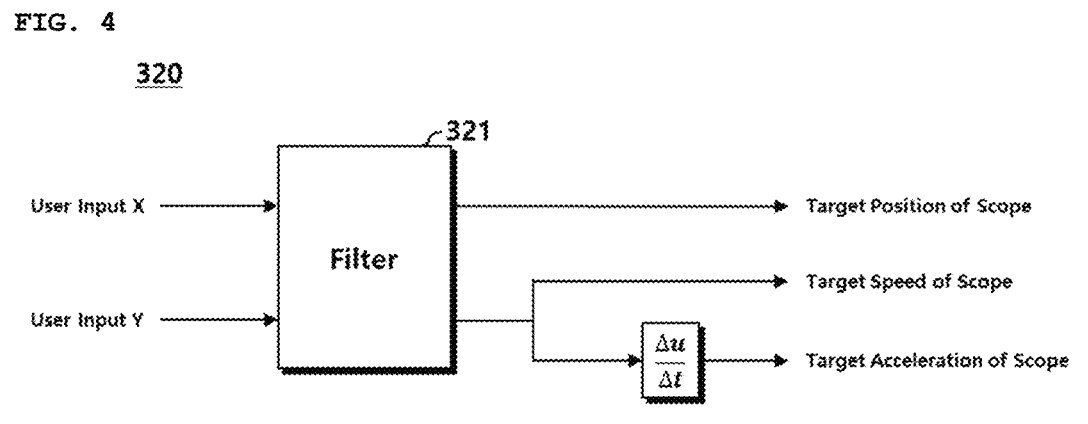

User Input X ⟶ Filter

User Input Y ⟶

⟶ Target Position of Scope

⟶ Target Speed of Scope $\dfrac{\Delta u}{\Delta t}$

⟶ Target Acceleration of Scope

Figure 5:
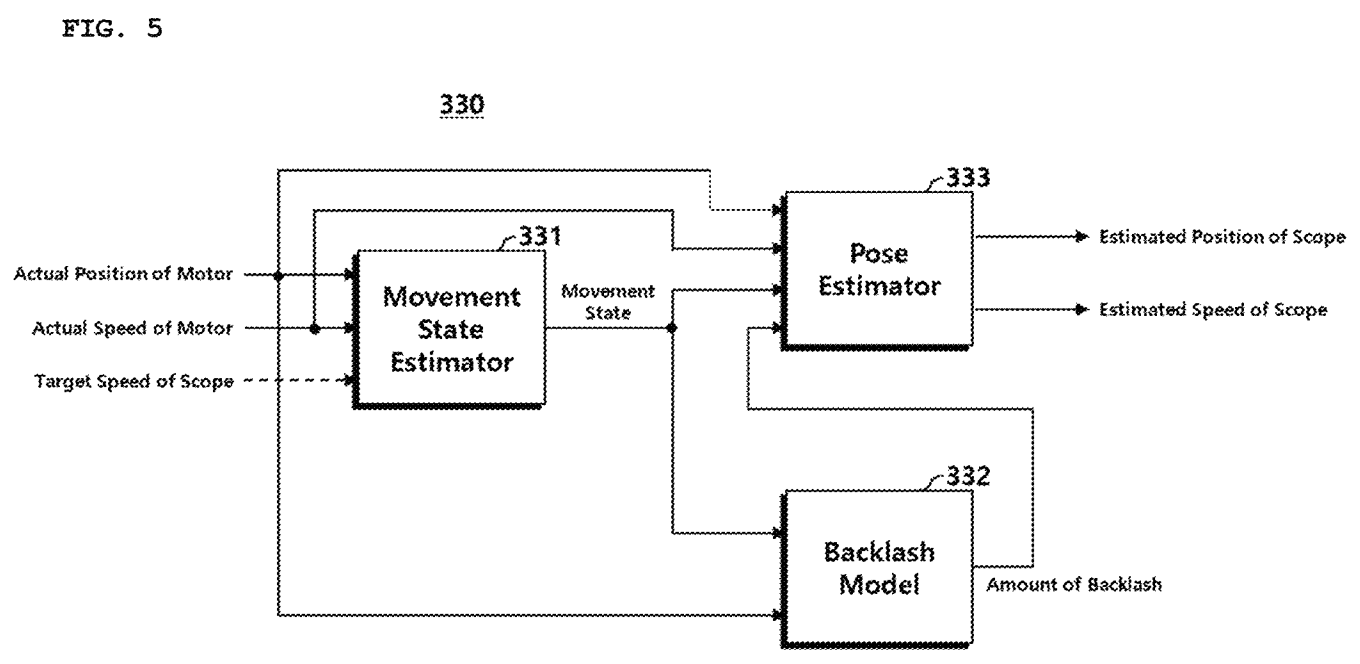

Estimated Position of Scope

Estimated Speed of Scope

333 Pose Estimator

Amount of Backlash

332 Backlash Model

Movement State

331 Movement State Estimator

Actual Position of Motor

Actual Speed of Motor

Target Speed of Scope

FIG. 6

METHOD, PROGRAM, AND APPARATUS FOR CONTROLLING ENDOSCOPE DEVICE

CROSS-REFERENCE TO RELATED APPLICATION

This application claims the benefit of Korean Patent Application No. 10-2023-0177321 filed on Korean Intellectual Property Office, which is hereby incorporated by reference herein in its entirety.

BACKGROUND

1. Technical Field

The present disclosure relates to endoscope control technology, and more particularly, to a method, computer program, and apparatus for controlling a motor for the movement of the scope of an endoscope device.

2. Description of the Related Art

Endoscopes collectively refer to medical devices that enable a scope to be inserted into the human body and a user to observe an organ without surgery or autopsy. Endoscopes enable a scope to be inserted into the body, radiate light, and visualize the light reflected from the surface of the inner wall of the body. Endoscopes are classified according to their purpose and target body part, and may be basically classified into rigid endoscopes, in which an endoscopic tube is made of metal, and flexible endoscopes, which are represented by digestive endoscopes.

A flexible endoscope contains various devices therein and is thus vulnerable to impact, and also the inside of a digestive organ into which a flexible endoscope is inserted corresponds to a considerably fragile tissue and has an irregular shape. Furthermore, the shape of the inside of the digestive organ varies depending on the patient, so that the process of inserting the endoscope may not be easy even for experienced medical professionals.

In this case, as an endoscopic procedure is performed, an endoscopic scope is inserted into a digestive organ while being twisted and turned according to the shape of the digestive organ. In the early stage of the endoscopic procedure, an endoscopic operator may bend or move the scope to a desired angle without a large amount of force because the scope has a relatively simple shape. However, as the procedure progresses to the latter half of the procedure or when complex movement is involved during the procedure, controlling the scope while taking into consideration the characteristics of the scope that may change at any moment can cause significant inconvenience to the endoscopic operator.

In addition, the nature of the endoscopic procedure in which the scope is inserted into the body requires the delicate control of the scope, and thus, there is a demand for technology for controlling an endoscopic scope by reflecting therein the physical changes that occur in an endoscope device during an endoscopic procedure.

RELATED ART LITERATURE

Patent Literature
Korean Patent No. 10-1940046 (published on Jan. 18, 2019)

SUMMARY

The present disclosure is intended to overcome the problems of the above-described conventional art, and is directed to a method, computer program, and apparatus for controlling the motor of an endoscope device so that the scope of the endoscope device can move to a position desired by a user at a speed also desired by the user.

However, objects to be achieved by the present disclosure are not limited to the object described above, and another object may be present.

According to one embodiment of the present disclosure for achieving the above-described object, there is disclosed a method of controlling an endoscope scope, which is performed by a computing device including at least one processor. The method includes: obtaining first data regarding the actual movement state of a motor included in an endoscope device and second data regarding the target movement state of a scope included in the endoscope device; and controlling the motor based on the obtained first data and second data.

Alternatively, the actual movement state of the motor may include at least one of the actual position of the motor and actual speed of the motor, which are measured by a sensor.

Alternatively, the target movement state of the scope may include at least one of the target position of the scope, target speed of the scope, and target acceleration of the scope, which are computed via the endoscopic device.

Alternatively, controlling the motor based on the obtained first data and second data may include: obtaining third data regarding the estimated movement state of the scope based on the obtained first data and second data; and computing a torque for controlling the motor based on the obtained first data, second data, and third data.

Alternatively, the estimated motion state of the scope may include at least one of the estimated position of the scope and estimated speed of the scope, which are computed based on the actual position data of the motor included in the first data and the actual speed data of the motor included in the first data.

Alternatively, obtaining the third data regarding the estimated movement state of the scope includes: determining whether backlash for the scope has occurred based on the actual position data of the motor included in the first data and the actual speed data of the motor included in the first data; and generating the third data based on the actual position data of the motor, the actual speed data of the motor, and first compensation data regarding the amount of occurred backlash, which is determined based on whether the backlash for the scope has occurred.

Alternatively, the torque may include: a first torque for controlling the motor so that the scope follows a position and speed desired by a user; and a second torque for minimizing an error caused in control based on the first torque.

Alternatively, the first torque may be computed using a first controller including a mathematical model that uses the second data and the third data as input variables.

Alternatively, the mathematical model included in the first controller may include sliding mode control.

Alternatively, the second torque may be computed using a second controller including a mathematical model that uses the first data and the second data as input variables.

Alternatively, the mathematical model included in the second controller may include a nonlinear compensator.

Alternatively, controlling the motor based on the obtained first data and second data may include computing the position of the motor based on the target position data of the motor determined by the second data and second compensation data regarding the amount of occurred backlash, which is determined based on whether backlash for the scope has occurred.

Alternatively, the second compensation data may be a combination of an estimated value regarding the amount of occurred backlash computed based on the first data and a current state value at the time when the backlash occurs.

Alternatively, the second compensation data may be updated whenever the backlash occurs.

According to one embodiment of the present disclosure for achieving the above-described object, there is disclosed a computer program that is stored in a computer-readable storage medium and, when executed on at least one processor, causes the processor to perform operations for controlling an endoscope scope. The operations include operations of: obtaining first data regarding the actual movement state of a motor included in an endoscope device and second data regarding the target movement state of a scope included in the endoscope device; and controlling the motor based on the obtained first data and second data.

According to one embodiment of the present disclosure for achieving the above-described object, there is disclosed a computing device for controlling an endoscopic scope. The computing device includes a processor including at least one core and memory including program codes executable on the processor, and the processor obtains first data regarding the actual movement state of a motor included in an endoscope device and second data regarding the target movement state of a scope included in the endoscope device and controls the motor based on the obtained first data and second data.

According to one embodiment of the present disclosure, precise and minute scope control may be achieved by controlling the position, speed, and torque of a motor so that the scope of an endoscope device follows the position and speed desired by a user. That is, the error between the manipulation of the user and the movement of the scope is reduced, so that the convenience and satisfaction of an endoscopic procedure can be increased and a sense of stability can be provided to a patient during an endoscopic procedure.

BRIEF DESCRIPTION OF THE DRAWINGS

The above and other objects, features, and advantages of the present invention will be more clearly understood from the following detailed description taken in conjunction with the accompanying drawings, in which:

FIG. 4 is a block diagram of a manipulation portion according to one embodiment of the present disclosure;

FIG. 5 is a block diagram of a scope estimation model according to one embodiment of the present disclosure;

FIG. 6 is a block diagram of a first controller according to one embodiment of the present disclosure;

DETAILED DESCRIPTION

Figure 1:
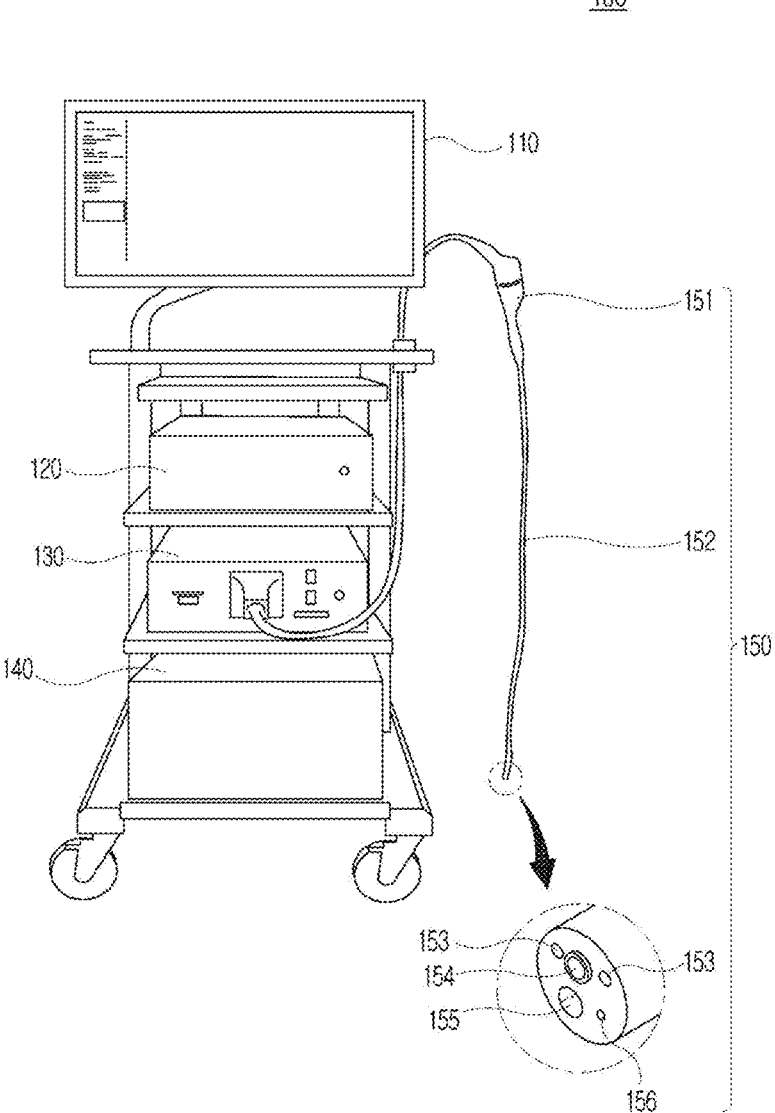
FIG. 1 is a diagram showing the configuration of endoscope device according to one embodiment of the present disclosure.

Embodiments of the present disclosure will be described in detail below with reference to the accompanying drawings so that those having ordinary skill in the art of the present disclosure (hereinafter referred to as those skilled in the art) can easily implement the present disclosure. The embodiments presented in the present disclosure are provided to enable those skilled in the art to use or practice the content of the present disclosure. Accordingly, various modifications to embodiments of the present disclosure will be apparent to those skilled in the art. That is, the present disclosure may be implemented in various different forms and is not limited to the following embodiments.

The same or similar reference numerals denote the same or similar components throughout the specification of the present disclosure. Additionally, in order to clearly describe the present disclosure, reference numerals for parts that are not related to the description of the present disclosure may be omitted in the drawings.

The term "or" used herein is intended not to mean an exclusive "or" but to mean an inclusive "or." That is, unless otherwise specified herein or the meaning is not clear from the context, the clause "X uses A or B" should be understood to mean one of the natural inclusive substitutions. For example, unless otherwise specified herein or the meaning is not clear from the context, the clause "X uses A or B" may be interpreted as any one of a case where X uses A, a case where X uses B, and a case where X uses both A and B.

The term "and/or" used herein should be understood to refer to and include all possible combinations of one or more of listed related concepts.

The terms "include" and/or "including" used herein should be understood to mean that specific features and/or components are present. However, the terms "include" and/or "including" should be understood as not excluding the presence or addition of one or more other features, one or more other components, and/or combinations thereof.

Unless otherwise specified herein or unless the context clearly indicates a singular form, a singular form should generally be construed to include "one or more."

The term "N-th (N is a natural number)" used herein can be understood as an expression used to distinguish the components of the present disclosure according to a predetermined criterion such as a functional perspective, a structural perspective, or the convenience of description. For example, in the present disclosure, components performing different functional roles may be distinguished as a first component or a second component. However, components that are substantially the same within the technical spirit of the present disclosure but should be distinguished for the convenience of description may also be distinguished as a first component or a second component.

Meanwhile, the term "module" or "unit" used herein may be understood as a term referring to an independent functional unit that processes computing resources, such as a computer-related entity, firmware, software or part thereof, hardware or part thereof, or a combination of software and hardware. In this case, the "module" or "unit" may be a unit composed of a single component, or may be a unit expressed as a combination or set of multiple components. For example, in the narrow sense, the term "module" or "unit" may refer to a hardware component or set of components of a computing device, an application program performing a specific function of software, a procedure implemented through the execution of software, a set of instructions for the execution of a program, or the like. Additionally, in the broad sense, the term "module" or "unit" may refer to a computing device itself constituting part of a system, an application running on the computing device, or the like. However, the above-described concepts are only examples, and the concept of "module" or "unit" may be defined in various manners within a range understandable to those skilled in the art based on the content of the present disclosure.

The term "model" used herein may be understood as a system implemented using mathematical concepts and language to solve a specific problem, a set of software units intended to solve a specific problem, or an abstract model for a process intended to solve a specific problem. For example, a neural network "model" may refer to an overall system implemented as a neural network that is provided with problem-solving capabilities through training. In this case, the neural network may be provided with problem-solving capabilities by optimizing parameters connecting nodes or neurons through training. The neural network "model" may include a single neural network, or a neural network set in which multiple neural networks are combined together.

The term "obtaining" used herein may be understood to mean not only receiving data over a wired/wireless communication network with an external device or system, but also generating data in an on-device form.

The foregoing descriptions of the terms are intended to help to understand the present disclosure. Accordingly, it should be noted that unless the above-described terms are explicitly described as limiting the content of the present disclosure, the terms in the content of the present disclosure are not used in the sense of limiting the technical spirit of the present disclosure.

FIG. 1 is a diagram showing the configuration of endoscope device according to one embodiment of the present disclosure.

Referring to FIG. 1, an endoscope device 100 according to one embodiment of the present disclosure may be a flexible endoscope, or more specifically, a digestive endoscope. The endoscope device 100 may include a configuration capable of obtaining a medical image adapted to photograph the inside of a digestive organ and a configuration capable of, when necessary, allowing a tool to be inserted and a user to perform treatment or manipulation while viewing a medical image.

The endoscope device 100 may include an output unit 110, a control unit 120, a drive unit 130, a pump unit 140, and a scope 150, and may further include a light source unit (not shown).

The output unit 110 may include a display configured to display medical images. The output unit 110 may include a display module configured to output visualized information or implement touch screens, such as a liquid crystal display (LCD), a thin film transistor-liquid crystal display (TFT LCD), an organic light-emitting diode (OLED), a flexible display, a three-dimensional (3D) display, or the like.

Figure 2:
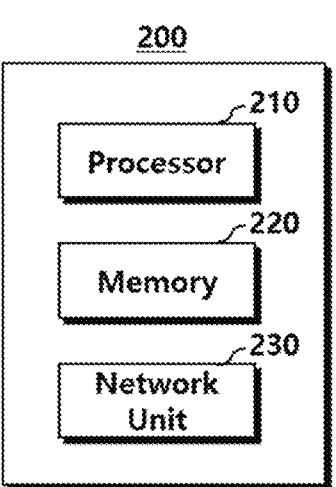
FIG. 2 is a block diagram showing a computing device according to one embodiment of the present disclosure.

The output unit 110 may include various means for providing medical images or information about medical images. The output unit 110 may display medical images obtained by the scope 150 or medical images processed by the control unit 120. The output unit 110 may provide information through an auditory means in addition to a visual means, and may include, for example, a speaker configured to provide alarms regarding medical images audibly. Meanwhile, although the one output unit 110 is illustrated in FIG. 2, a plurality of output units 110 may be provided. In this case, an output unit 110 where a medical image obtained by the scope 150 is displayed and an output unit 110 where information processed by the control unit 120 is displayed may be separated from each other.

The control unit 120 may control the overall operation of the endoscope device 100. For example, the control unit 120 may perform the operation of taking a medical image through the scope 150, the operation of processing an obtained medical image, the control operation of performing medical operations such as the spraying of washing water, suction, or the like, a series of operations for controlling the movement of the scope 150, etc. The control unit 120 may include all types of devices capable of processing data. According to an exemplary embodiment, the control unit 120 may be a data processing device embedded in hardware that has circuits physically structured to perform the functions represented by the codes or instructions included in a program. As an example of the data processing device embedded in hardware, a processing device such as a microprocessor, a central processing unit (CPU), a processor core, a multiprocessor, an application-specific integrated circuit (ASIC), or a field programmable gate array (FPGA) may be included, but the technical spirit of the present disclosure is not limited thereto.

The control unit 120 may control the movement of the scope 150 through the drive unit 130 connected to the scope 150. That is, the control unit 120 may generate control signals to be provided to the drive unit 130 in order to control the movement of the scope 150.

For example, a series of operations in which the endoscope device 100 of the present disclosure controls the scope 150 may be performed as follows. A user may input the degree or direction of curvature of the scope 150 through a manipulation portion. The input information is transmitted to the control unit 120, and the control unit 120 may process the input information and generate a signal to be provided to the drive unit 130. For example, the control unit 120 may compute the position, angle, angular velocity, and/or like of a motor corresponding to the degree or direction of curvature set by the user and may provide them to the drive unit 130. The drive unit 130 may generate power based on the signal of the control unit 120 and transmit it to the scope 150. Accordingly, the scope 150 may be moved or bent in accordance with the value input by the user.

The drive unit 130 may provide power required for the scope 150 to be inserted into the body, bent, and moved inside the body. For example, the drive unit 130 may include the motor connected to the wire inside the scope 150 and a tension adjustment unit configured to adjust the tension of the wire.

The drive unit 130 may control the scope 150 in various directions by controlling the power of the motor. For example, the motor may be configured to include a plurality of motors corresponding to the directions in which the insertion portion at the end of the scope 150 is to be bent. Alternatively, the motor may be configured to include a plurality of motors corresponding to wires inside the scope 150. More specifically, the drive unit 130 may include a first motor configured to determine the x-axis movement of the scope 150 and a second motor configured to determine the y-axis movement of the scope 150. The x-axis position, y-axis position, z-axis position, roll, pitch, and yaw values of the end of the scope 150 may be determined according to the control of the drive unit 130, but the configuration of the drive unit 130 is not limited thereto.

The tension adjustment unit may receive power from the motor and pull the wire inside the scope 150 to generate tension. Through this, the scope 150 may be bent. The tension adjustment unit may adjust the tension applied to the plurality of wires 1000 inside the scope 150 so that the scope 150 can be bent according to the determined amount and direction of bending.

The pump unit 140 may include at least one of an air pump configured to inject air into the human body through the scope 150, a suction pump configured to provide negative pressure or vacuum and suck air from the body through the scope 150, and a water pump configured to inject cleaning water into the body through the scope 150. Each of the pumps may include a valve configured to control the flow of fluid. The pump unit 140 may be opened and closed by the control unit 120. At least one of the suction pump, the water pump, and the air pump may be opened and closed based on a control signal of a computing device or the control of the control unit 120.

The scope 150 may include the insertion portion 152 configured to be inserted into a digestive organ and the operating portion 151 configured to control the movement of the insertion portion 152 and receive input from a user to perform various operations.

The insertion portion 152 is configured to be flexibly bent and is connected to the drive unit 130 at one end thereof, so that the degree or direction of curvature can be determined by the drive unit 130. Since medical imaging and treatment are performed at the end of the insertion portion 152, the scope 150 may include various cables and tubes that extend to the end of the insertion portion 152. A light source lens 153, an objective lens 154, a working channel 155, and an air and water channel 156 may be provided inside the scope 150. A tool for treating and managing a lesion may be inserted through the working channel 155 during an endoscopic procedure. Air may be injected and washing water may be fed through the air and water channel 156. Meanwhile, in FIG. 2, the air and water channel 156 is illustrated as a passage through which washing water is fed, but it is not limited thereto. For example, a separate water jet channel (not shown) may be provided inside the scope 150, and cleaning water may also be fed through a water jet channel.

Meanwhile, references herein to the scope 150 being bent by the control unit 120 or the drive unit 130 may refer to at least a part of the scope 150, e.g., the insertion portion 152, being bent.

The manipulation portion 151 may include a plurality of input buttons configure to provide various functions (image capture, the spray of cleaning water, etc.) to allow an endoscopic operator to control the steering of the insertion portion 152 and perform a procedure through the working channel 155 and the air and water channel 156. For example, the manipulation portion 151 may include a plurality of buttons or a joystick-type input device configured to indicate the direction of the scope 150.

The light source unit may include a light source that radiates light into the body through the endoscopic scope 150. The light source unit may include a lighting device configured to generate white light, or may include a plurality of lighting devices configured to generate rays of light having different wavelength bands. The type of light source, the intensity of light, white balance, and/or the like may be set through the light source unit. Meanwhile, the above-described setting items may also be set through the control unit 120. The light generated by the light source unit may be transmitted to the scope 150 through a path such as an optical fiber.

FIG. 2 is a block diagram showing a computing device according to one embodiment of the present disclosure.

The computing device 200 according to the one embodiment of the present disclosure may be a hardware device or part of a hardware device that performs the comprehensive processing and computation of data, or may be a software-based computing environment that is connected to a communication network. For example, the computing device 200 may be a dependent device that is built into an endoscope device and performs an intensive data processing function required for controlling the endoscope device. The computing device 200 may also be an independent device, such as a server, that performs an intensive data processing function required for controlling an endoscope device via wired/wireless communication with the endoscope device. Since the foregoing description is only one example related to the type of computing device 200, the type of computing device 200 may be configured in various manners within a range understandable to those skilled in the art based on the content of the present disclosure.

Referring to FIG. 2, the computing device 200 according to the one embodiment of the present disclosure may include a processor 210, memory 220, and a network unit 230. However, FIG. 2 illustrates only an example, and the computing device 200 may include other components for implementing a computing environment. Furthermore, only some of the components disclosed above may be included in the computing device 200.

The processor 210 according to one embodiment of the present disclosure may be understood as a constituent unit including hardware and/or software for performing computing operation. For example, the processor 210 may read a computer program and perform the processing of data obtainable in the process of controlling an endoscope device. The processor 210 for performing such data processing may include a central processing unit (CPU), a general purpose graphics processing unit (GPGPU), a tensor processing unit (TPU), an application specific integrated circuit (ASIC), or a field programmable gate array (FPGA). Since the types of processor 210 described above are only examples, the type of processor 210 may be configured in various manners within a range understandable to those skilled in the art based on the content of the present disclosure.

The processor 210 may compute the torque that causes the scope of the endoscope device to follow the position and speed desired by a user. Furthermore, the processor 210 may compute the position or speed of the motor. Moreover, the processor 210 may control the motor by inputting at least one of the computed torque and the computed position or speed of the motor. For example, when the end of the scope 150 and the drive unit 130 are separated by a specific distance or more as in the endoscope device 100 of FIG. 1, the power of the drive unit 130 may not be completely transmitted to the end of the scope 150 through the wire, and thus, an error may occur between a user's control command and the movement of the scope 150. The processor 210 may compute the torque required to reduce the error between the control command and the movement of the scope 150 or the position and speed of the motor by performing computation based on data regarding the target movement state of the scope 150 and data regarding the estimated movement state of the scope 150. That is, the processor 210 may control the position of the motor and the torque of the motor in parallel. In this case, the control for the position of the motor may be understood as control that takes into consideration kinematics. Furthermore, the control for the torque of the motor may be understood as control that takes into consideration dynamics.

The memory 220 according to one embodiment of the present disclosure may be understood as a constituent unit including hardware and/or software for storing and managing data that is processed in the computing device 200. That is, the memory 220 may store any type of data generated or determined by the processor 210 and any type of data received by the network unit 230. For example, the memory 220 may include at least one type of storage medium of a flash memory type, hard disk type, multimedia card micro type, and card type memory, random access memory (RAM), static random access memory (SRAM), read-only memory (ROM), electrically erasable programmable read-only memory (EEPROM), programmable read-only memory (PROM), magnetic memory, a magnetic disk, and an optical disk. Furthermore, the memory 220 may include a database system that controls and manages data in a predetermined system. Since the types of memory 220 described above are only examples, the type of memory 220 may be configured in various manners within a range understandable to those skilled in the art based on the content of the present disclosure.

The memory 220 may structure, organize, and manage data required for the processor 110 to perform computation, the combinations of data, and program codes executable on the processor 210. For example, the memory 220 may store program codes adapted to operate the processor 210 to compute torque using a mathematical model, and may also store various types of data generated as the program codes are executed. Furthermore, the memory 220 may store various types of data transmitted and received via the network unit 230 to be described below for use in the torque computation of the processor 210.

The network unit 230 according to one embodiment of the present disclosure may be understood as a constituent unit that transmits and receives data through any type of known wired/wireless communication system. For example, the network unit 230 may perform data transmission and reception using a wired/wireless communication system such as a local area (LAN), a wideband code division multiple access network (WCDMA) network, a long term evolution (LTE) network, the wireless broadband Internet (WiBro), a 5th generation mobile communication (5G) network, a ultra wide-band wireless communication network, a ZigBee network, a radio frequency (RF) communication network, a wireless LAN, a wireless fidelity network, a near field communication (NFC) network, or a Bluetooth network. Since the above-described communication systems are only examples, the wired/wireless communication system for the data transmission and reception of the network unit 230 may be applied in various manners other than the above-described examples.

Meanwhile, data to be processed by the processor 210 may be stored in the memory 220 or received via the network unit 230, and data generated by the processor 210 may be stored in the memory 220 or transmitted to the outside via the network unit 230.

Figure 3:
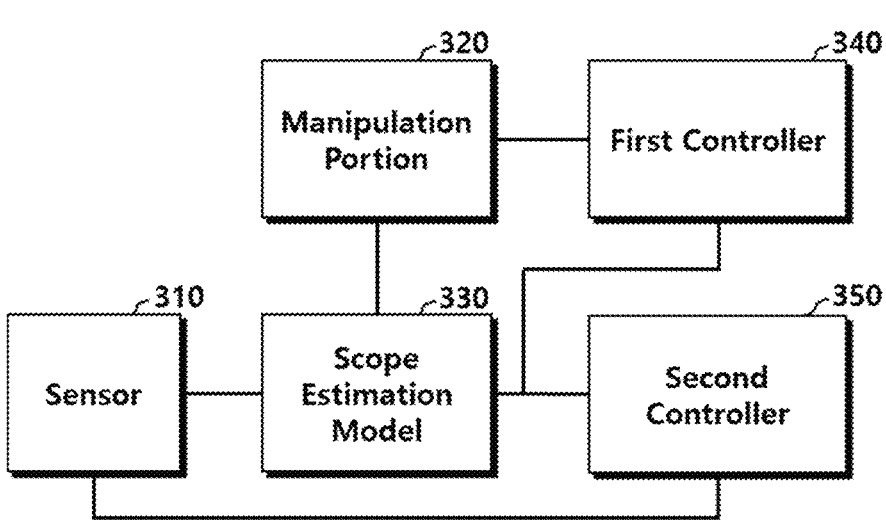
FIG. 3 is a block diagram of a configuration for control according to one embodiment of the present disclosure.

FIG. 3 is a block diagram of a configuration for control according to one embodiment of the present disclosure.

Referring to FIG. 3, the control according to the one embodiment of the present disclosure may be performed via a sensor 310 and manipulation portion 320 included in an endoscope device, and a scope estimation model 330, a first controller 340, and a second controller 350 implemented via the endoscope device or a computing device. When the computing device is provided in the endoscope device, the computing device may be understood as corresponding to the control unit of the endoscope device. Accordingly, when the computing device is provided in the endoscope device, the scope estimation model 330, the first controller 340, and the second controller 350 may be understood as software units that are implemented by the control unit. When the computing device is a device independent of the endoscope device, the computing device may obtain data, generated by the sensor 310 or manipulation portion 320, through wired/wireless communication with the endoscope device. Furthermore, the computing device may perform the computation required for control based on the data obtained from the sensor 310 or manipulation portion 320 via the scope estimation model 330, the first controller 340, and the second controller 350.

The sensor 310 may detect the actual movement of a motor included in the endoscope device and generate first data regarding the actual movement state of the motor. In this case, the actual movement state of the motor may include at least one of the actual position of the motor and the actual speed of the motor, which are measured by the sensor provided in the motor. That is, the sensor 310 may detect the position at which the motor is located or the speed at which the motor moves according to the movement of the motor. Then, the sensor 310 may generate first data regarding the actual movement state of the motor based on a detected value.

The manipulation portion 320 may receive user input and generate second data regarding the target movement state of the motor. In this case, the target movement state of the scope may include at least one of the target position of the scope, the target speed of the scope, and the target acceleration of the scope, which are generated through a command issued using a joystick included in the endoscope device. That is, the manipulation portion 320 may obtain a user command via the joystick. Furthermore, the manipulation portion 320 may generate second data indicating the position to which the scope will be moved and the speed or acceleration at which the scope will be moved in accordance with the user command.

The scope estimation model 330 may estimate the movement state of the scope based on the first data generated by the sensor 310 and the second data generated by the manipulation portion 320, and may generate third data regarding the estimated movement state of the scope. In this case, the estimated movement state of the scope may include at least one of the estimated position of the scope and the estimated speed of the scope, which are computed based on the actual position data of the motor included in the first data and the actual speed data of the motor included in the first data. In this case, the target speed data of the scope included in the second data may be used as a reference parameter for the computation of the estimated position or the estimated speed. That is, the scope estimation model 330 may compute an estimated value regarding the position to which the scope will be moved or the speed at which the scope will be moved based on the actual movement state of the motor and the target movement state of the scope, and may generate third data.

The first controller 340 may compute a first torque for the control of the motor based on the second data generated by the manipulation portion 320 and the third data generated by the scope estimation model 330. In this case, the first torque may play a role in controlling the motor so that the scope can follow the position and speed desired by a user. That is, the first controller 340 may compute the first torque input to the motor so that the scope can be accurately controlled according to the user's intention via a mathematical model that uses the second data and the third data as input variables. In this case, the mathematical model included in the first controller 340 may include sliding mode control.

The second controller 350 may compute a second torque for the control of the motor based on the first data and the third data. In this case, the second torque may play a role in minimizing the error caused in control based on the first torque. That is, the second controller 350 may compute the second torque that compensates for the error so that the control by the first torque can be accurately performed via a mathematical model that uses the first data and the second data as input variables. In this case, the mathematical model included in the second controller 350 may include a non-linear compensator.

FIG. 4 is a block diagram of a manipulation portion according to one embodiment of the present disclosure.

Referring to FIG. 4, the manipulation portion 320 according to the one embodiment of the present disclosure may receive user input via the joystick. In this case, the user input may be a command that determines how the scope will move. The manipulation portion 320 may compute the target position of the scope and the target speed of the scope based on the user input via a filter 321. In this case, the filter 321 may be a moving average filter or a Kalman filter, but the present disclosure is not limited thereto. Furthermore, the manipulation portion 320 may compute the target accelera- tion of the scope through additional computation for the target speed of the scope computed via the filter 321. That is, the manipulation portion 320 may compute the target position of the scope, the target speed of the scope, and the target acceleration of the scope based on the user input.

FIG. 5 is a block diagram of a scope estimation model according to one embodiment of the present disclosure.

Referring to FIG. 5, the scope estimation model 330 according to the one embodiment of the present disclosure may receive the actual position and actual speed of the motor measured via the sensor 310, and the target speed of the scope computed via the manipulation portion 320. The scope estimation model 330 may estimate the movement state of the scope by entering the actual position and actual speed of the motor to a movement state estimator 331. In this case, the target speed of the scope may be used as a reference parameter for the estimation of the movement state. Fur- thermore, the movement state of the scope may include information about whether compensation for backlash is required. In other words, the scope estimation model 330 may determine whether backlash has occurred via the move- ment state estimator 331.

The scope estimation model 330 may compute the amount of backlash based on the movement state of the scope estimated by the movement state estimator 331 and the actual position of the motor measured by the sensor 310. More specifically, when it is determined via the movement state estimator 331 that backlash has occurred, the scope estimation model 330 may compute the amount of backlash by entering the actual position of the motor to a backlash model 332. In this case, the backlash model 332 may be a model generated by modeling the tendency of the amount of backlash that has occurred based on the actual position of the motor and the estimated position of the motor. When it is determined via the movement state estimator 331 that back- lash has not occurred, the scope estimation model 330 may not perform the operation of the backlash model 332.

The scope estimation model 330 may compute the esti- mated position and estimated speed of the scope based on the actual position and actual speed of the motor measured via the sensor 310 and the amount of backlash computed via the backlash model 332. More specifically, the scope esti- mation model 330 may compute the estimated position and estimated speed of the scope by entering the actual position and actual speed of the motor and the amount of backlash to a pose estimator 333. In this case, when it is determined via the movement state estimator 331 that backlash has occurred, the pose estimator 333 determines that when the backlash occurs, the angle of the motor changes but the angle of the scope does not change, and thus can estimate the position of the scope before the occurrence of the backlash as the current position of the scope at the time when the backlash has occurred. In contrast, when it is determined via the motion state estimator 331 that backlash has not occurred, the pose estimator 333 may estimate the current position of the scope where backlash has not occurred by utilizing the maximum angle of the motor corresponding to the maximum angle of the scope. Furthermore, the pose estimator 333 may compute the estimated speed of the scope based on the change in the estimated position of the scope. Meanwhile, the pose estimator 333 may also perform an operation based on a machine learning model. In this case, the machine learning model may be a model pre-learned to perform time-series prediction that computes the estimated position of the scope based on the actual position of the motor, the actual speed of the motor, and the amount of backlash. For example, the machine learning model may include a multi-layer perceptron (MLP), a vanilla recurrent neural network (RNN), a long-short term memory (LSTM), etc.

Figure 6:
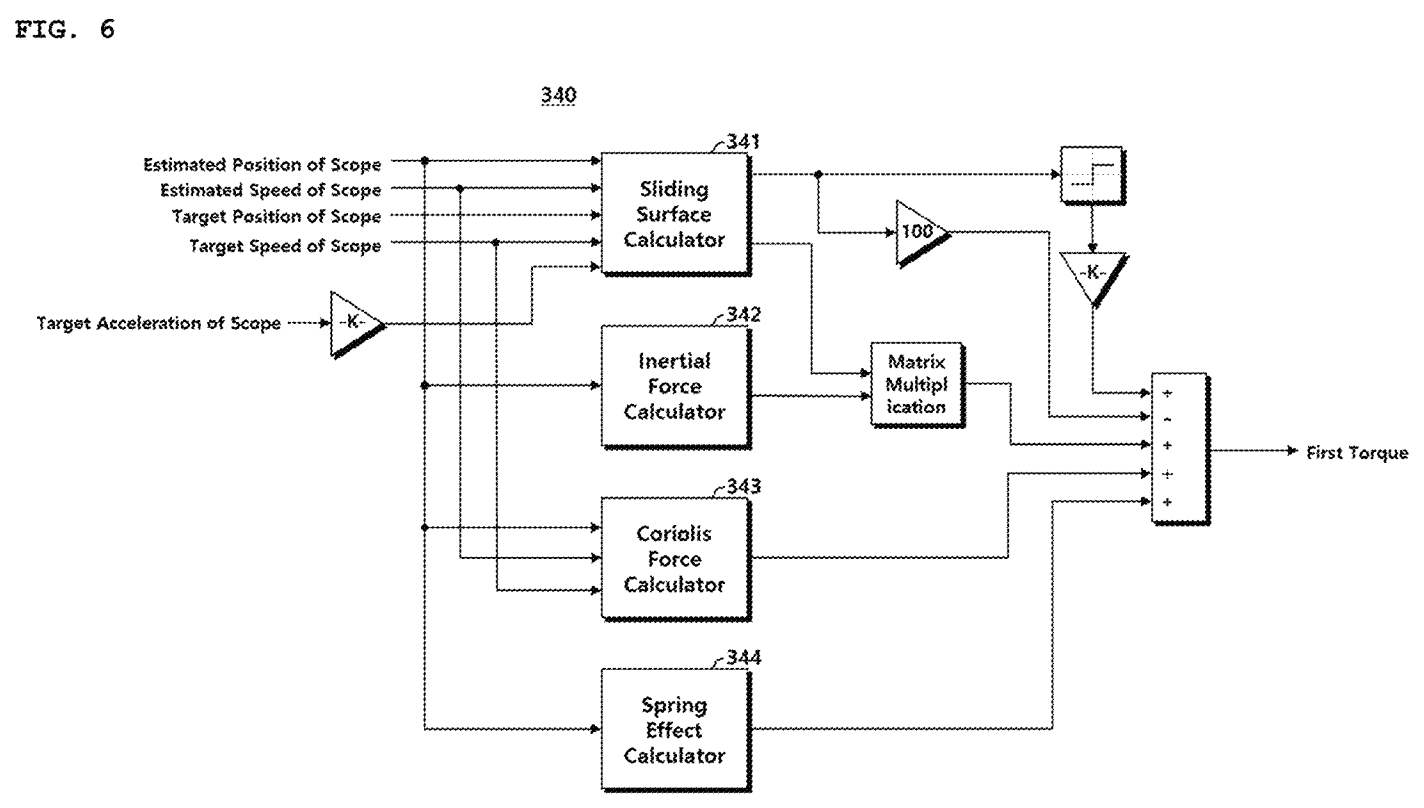

FIG. 6 is a block diagram of a first controller according to one embodiment of the present disclosure.

Referring to FIG. 6, the first controller 340 according to one embodiment of the present disclosure may receive the estimated position and estimated velocity of the scope computed via the scope estimation model 330 and the target position and target velocity of the scope computed via the manipulation portion 320. The first controller 340 may compute the sliding surface based on the estimated position and estimated velocity of the scope and the target position, target velocity, and target acceleration of the scope using a sliding surface calculator 341. The first controller 340 may compute the inertial force based on the estimated position of the scope using an inertial force calculator 342. The first controller 340 may compute the Coriolis force based on the estimated position, estimated velocity, and target velocity of the scope using a Coriolis force calculator 343. The first controller 340 may compute the force attributable to the shape of the scope based on the estimated position of the scope using a spring effect calculator 344. Furthermore, the first controller 340 may compute a first torque to be input to the motor for the purpose of movement control of the scope according to the user's intention by performing additional operations based on the values computed via the respective calculators 341, 342, 343, and 344. In this case, the first torque computed by the computation of the first controller 340 may be represented by Equation 1 below:

$$\tau = M(\ddot{q}_d - \lambda(\dot{q} - \dot{q}_d)) - \tag{1}$$
$$M(M+K)^{-1}\left(C + \frac{1}{2}\dot{K}\right)((\dot{q} - \dot{q}_d) + \lambda(q - q_d)) + C\dot{q} + K - \rho\mathrm{sign}(s) - \eta s$$

In Equation 1, M denotes the inertial force, C denotes the Coriolis force, and K denotes the force attributable to the shape of the spring. Furthermore, q denotes the estimated position of the scope, $\dot{q}$ denotes the estimated velocity of the scope, $q_d$ denotes the target position of the scope, $\dot{q}_d$ denotes the target velocity of the scope, and $\ddot{q}_d$ denotes the target acceleration of the scope. Furthermore, $-\rho$ sign(s) denotes a value used to compensate for the maximum value of uncer- tainty, and $-\eta s$ denotes a value used to reduce the tracking error that may occur because the derivative of the Lyapunov function may become 0 when the maximum disturbance is compensated for. The first controller 340 may compute the first torque that can minimize the end tracking error that may occur during the control process of the scope through a combination of the calculators 341, 342, 343, and 344 in which the physical characteristics of the endoscope device corresponding to Equation 1 are reflected.

Figure 7:
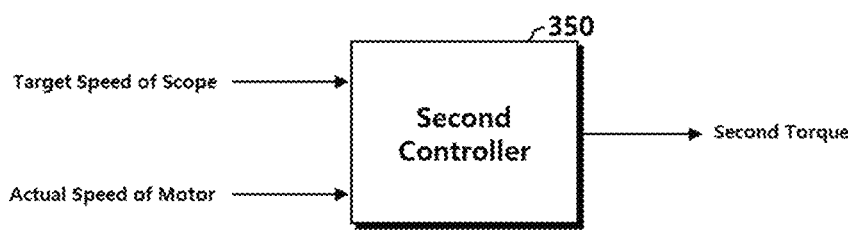
FIG. 7 is a block diagram of a second controller according to one embodiment of the present disclosure.

FIG. 7 is a block diagram of a second controller according to one embodiment of the present disclosure.

Referring to FIG. 7, the second controller 350 according to the one embodiment of the present disclosure may obtain the speed of the motor measured via the sensor 310 and the actual target speed of the scope generated via the manipulation portion 320. The second controller 350 may generate a second torque used to compensate for the friction caused by a wire inside the scope and the friction between the motor and a gear based on the target speed of the scope and the actual speed of the motor. In this case, the second controller 350 may generate the second torque by performing modeling for the Coulomb-viscous friction and modeling for the Stribeck friction.

Meanwhile, in addition to the torque control of the motor performed through the first and second torques, the position control of the motor may be performed. Unlike the torque control, the position control of the motor may be understood as a kinematic-based control that focuses on moving the motor to a desired position without taking into consideration the force or friction attributable to the spring shape of the wire of the endoscope.

The position control of the motor may be performed based on the target position of the motor, determined based on the estimated position of the scope computed by the manipulation portion 320, and a backlash state. In this case, the backlash state may include the estimated value of the amount of backlash computed based on the backlash model 332 when the backlash occurs and the current angle at the time when the backlash occurs. For example, the computation of the position for the position control of the motor may be represented by Equation 2 below:

$$\theta_u^{ref} = \theta_m^{ref} + \theta_b^{ref} \tag{2}$$

where $$\theta_u^{ref}$$

denotes the position computed for control, $$\theta_m^{ref}$$

denotes the target position of the motor determined based on a user command, and $$\theta_b^{ref}$$

denotes the backlash state. Furthermore, $$\theta_b^{ref}$$

14 may be represented by Equation 3 below:

$$\theta_b^{ref} = \frac{\theta_b^{limit}}{2}\left(1 - \cos\left(\frac{pi}{f}t\right)\right) + \theta_b^{init} \tag{3}$$

where $$\theta_b^{limit}$$

denotes a value derived through the backlash model 332, $$\theta_b^{init}$$

denotes a current backlash angle, and f denotes a cycle determined according to the compensation time desired by the user. Furthermore, $$\theta_b^{limit},$$

t, and $$\theta_b^{init}$$

may be updated whenever backlash occurs.

That is, the position control of the motor of the present disclosure may be performed according to the position of the motor computed based on Equations 2 and 3 above. The present disclosure may rapidly compensate for the value caused by the occurrence of backlash within a predetermined period of time in a situation where backlash occurs through the position control, and may enable the scope to move again under the user's command.

Figure 8:
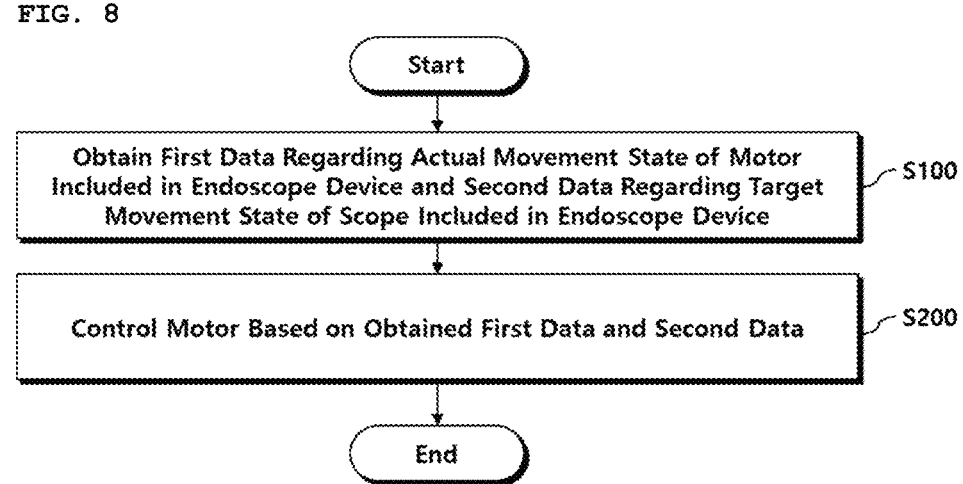
FIG. 8 is a flowchart showing a method of controlling an endoscope device according to one embodiment of the present disclosure.

FIG. 8 is a flowchart showing a method of controlling an endoscope device according to one embodiment of the present disclosure.

Referring to FIG. 8, the computing device according to one embodiment of the present disclosure may obtain first data regarding the actual movement state of a motor included in an endoscope device and second data regarding the target movement state of a scope included in the endoscope device in step S100. In this case, the first data may include at least one of the actual position data of the motor and the actual speed data of the motor, which are measured by the sensor. Furthermore, the second data may include at least one of the target position data of the scope, the target speed data of the scope, and the target acceleration data of the scope, which are computed via the endoscope device. When the computing device is a component dependent on the endoscope device, the computing device may correspond to the control unit of the endoscope device. When the computing device is a device independent of the endoscope device, the computing device may receive the first data and the second data through wired/wireless communication with the endoscope device.

In step S200, the computing device may control the motor based on the first data and the second data obtained through step S100. In this case, the control of the motor may be divided into torque control and position control. In order to control the torque of the motor, the computing device may obtain third data regarding the estimated movement state of the scope based on the first data and the second data. More specifically, the computing device may determine whether backlash for the scope has occurred based on the actual position data of the motor included in the first data and the actual speed data of the motor included in the first data. Furthermore, the computing device may generate the third data based on the actual position data of the motor, the actual speed data of the motor, and first compensation data regarding the amount of occurred backlash that is determined based on whether backlash has occurred. Once the third data has been generated, the computing device may compute the torque required for controlling the motor based on the first data, the second data, and the third data. A description of a specific computational process for controlling the torque of the motor is replaced by the description made in conjunction with FIGS. 3 to 7.

In order to perform the position control of the motor, the computing device may compute the position of the motor based on the target position data of the motor that is determined by the second data and the second compensation data regarding the amount of occurred backlash that is determined based on whether backlash for the scope has occurred. In this case, the target position data of the motor may be determined by the target position data of the scope included in the second data. Furthermore, the second compensation data may be a combination of an estimated value regarding the amount of occurred backlash computed based on the first data and a current state value at the time when backlash has occurred. A description of a specific computational process for performing the position control of the motor is replaced by the description made in conjunction with Equations 2 and 3 above.

The description of the present disclosure described above is intended for illustrative purposes, and those of ordinary skill in the art to which the present disclosure pertains can appreciate that the present disclosure may be easily modified into other specific forms without changing the technical spirit or essential features of the present disclosure. Therefore, it should be understood that the embodiments described above are illustrative and not restrictive in all respects. For example, each component described as being in a single form may be implemented in a distributed form. In the same manner, components described as being in a distributed form may be implemented in a combined form.

What is claimed is:

1. A method of controlling a flexible endoscope device having a scope insertable into a human body and being configured to observe an organ inside the human body, the method being performed by a processor, the method comprising:

obtaining first data regarding an actual movement state of the motor of the endoscope device;

obtaining second data regarding a target movement state of the scope of the endoscope device, the second data corresponding to and determined, in real time, by an input value received from the user input device; and controlling the motor based on the obtained first data and second data to adjust the motion of the scope substantially in real time based on the obtained first data, wherein controlling the motor based on the obtained first data and second data comprises:

obtaining third data regarding an estimated movement state of the scope using a motor-scope motion estimation model based on the obtained first and second data, wherein the motor-scope motion estimation model is a model that generates the estimated movement state of the scope as output upon receiving the obtained first data regarding the actual movement state of the motor and the obtained second data regarding the target movement state of the scope as input, wherein the motor-scope motion estimation model includes a backlash model, the backlash model being a model that, when the motor-scope motion estimation model determines that a backlash has occurred, generates an amount of backlash based on the obtained first data regarding the actual movement state of the motor;

computing, by a first controller, a first torque for controlling the motor, wherein the first torque for controlling the motor is determined based on the obtained first data regarding the actual movement state of the motor, the obtained second data regarding the target movement state of the scope, and the third data regarding the estimated movement state of the scope;

computing, by a second controller which is a friction compensation model, a second torque which compensates for a friction between the motor and a gear, wherein the friction compensation model includes a nonlinear compensator that generates the second torque as output upon receiving the obtained first data regarding the actual movement state of the motor and the obtained second data regarding the target movement state of the scope as input; and controlling the motion of the scope according to the determined first torque and the second torque.

2. The method of claim 1, wherein the actual movement state of the motor includes at least one of an actual position of the motor and actual speed of the motor, which are measured by a sensor.

3. The method of claim 1, wherein the target movement state of the scope includes at least one of a target position of the scope, target speed of the scope, and target acceleration of the scope, which are computed via the endoscope device.

4. The method of claim 1, wherein the estimated movement state of the scope includes at least one of an estimated position of the scope and estimated speed of the scope, which are computed based on actual position data of the motor included in the first data and actual speed data of the motor included in the first data.

5. The method of claim 1, wherein obtaining the third data regarding the estimated movement state of the scope comprises:

determining whether backlash for the scope has occurred based on actual position data of the motor included in the first data and actual speed data of the motor included in the first data; and generating the third data based on the actual position data of the motor, the actual speed data of the motor, and first compensation data regarding the amount of backlash, which is determined based on whether the backlash for the scope has occurred.

6. The method of claim 1, wherein the first torque for controlling the motor is determined so that the scope follows a target position and a target speed in the second data regarding the target movement state of the scope.

7. The method of claim 6, wherein the first torque is computed using the first controller including a mathematical model that uses the second data and the third data as input variables.

8. The method of claim 7, wherein the mathematical model included in the first controller includes sliding mode control.

9. The method of claim 1, wherein controlling the motor based on the obtained first data and second data comprises computing a position of the motor based on target position data of the motor determined by the second data and second compensation data regarding an amount of occurred backlash, which is determined based on whether backlash for the scope has occurred.

10. The method of claim 9, wherein the second compensation data is a combination of an estimated value regarding the amount of occurred backlash computed based on the first data and a current state value at a time when the backlash occurs.

11. The method of claim 9, wherein the second compensation data is updated whenever the backlash occurs.

12. A computer program stored in a computer-readable storage medium, the computer program, when executed on at least one processor, causing the processor to perform operations for controlling a flexible endoscope device having a scope insertable into a human body and being configured to observe an organ inside the human body, wherein the operations comprise operations of:

obtaining first data regarding an actual movement state of the motor of the endoscope device;

obtaining second data regarding a target movement state of the scope of the endoscope device, the second data corresponding to and determined, in real time, by an input value received from the user input device; and controlling the motor based on the obtained first data and second data to adjust the motion of the scope substantially in real time based on the obtained first data, wherein controlling the motor based on the obtained first data and second data comprises:

obtaining third data regarding an estimated movement state of the scope using a motor-scope motion estimation model based on the obtained first data and second data, wherein the motor-scope motion estimation model is a model that generates the estimated movement state of the scope as output upon receiving the obtained first data regarding the actual movement state of the motor and the obtained second data regarding the target movement state of the scope as input, wherein the motor-scope motion estimation model includes a backlash model, the backlash model being a model that, when the motor-scope motion estimation model determines that a backlash has occurred, generates an amount of backlash based on the obtained first data regarding the actual movement state of the motor;

computing, by a first controller, a first torque for controlling the motor, wherein the first torque for controlling the motor is determined based on the obtained first data regarding the actual movement state of the motor, the obtained second data regarding the target movement state of the scope, and the third data regarding the estimated movement state of the scope;

computing, by a second controller which is a friction compensation model, a second torque which compensates for a friction between the motor and a gear, wherein the friction compensation model includes nonlinear compensator that generates the second torque as output upon receiving the obtained first data regarding the actual movement state of the motor and the obtained second data regarding the target movement state of the scope as input; and controlling the motion of the scope according to the determined first torque and the second torque.

13. A computing device for controlling a flexible endoscope device having a scope insertable into a human body and being configured to observe an organ inside the human body, the computing device comprising:

a processor including at least one core; and a memory including program codes executable on the processor;

wherein the processor, when executing the program codes, is configured to perform:

obtaining first data regarding an actual movement state of the motor of the endoscope device;

obtaining second data regarding a target movement state of the scope of the endoscope device, the second data corresponding to and determined, in real time, by an input value received from the user input device; and controlling the motor based on the obtained first data and second data to adjust the motion of the scope substantially in real time based on the obtained first data, wherein the processor is further configured to perform, in controlling the motor based on the obtained first data and second data;

obtaining third data regarding an estimated movement state of the scope using a motor-scope motion estimation model based on the obtained first data and second data, wherein the motor-scope motion estimation model is a model that generates the estimated movement state of the scope as output upon receiving the obtained first data regarding the actual movement state of the motor and the obtained second data regarding the target movement state of the scope as input, wherein the motor-scope motion estimation model includes a backlash model, the backlash model being a model that, when the motor-scope motion estimation model determines that a backlash has occurred, generates an amount of backlash based on the obtained first data regarding the actual movement state of the motor;

computing, by a first controller, a first torque for controlling the motor, wherein the first torque for controlling the motor is determined based on the obtained first data regarding the actual movement state of a motor, the obtained second data regarding the target movement state of the scope, and the third data regarding the estimated movement state of the scope;

computing, by a second controller which is a friction compensation model, a second torque which compensates for a friction between the motor and a gear, wherein the friction compensation model includes nonlinear compensator that generates the second torque as output upon receiving the obtained first data regarding the actual movement state of the motor and the obtained second data regarding the target movement state of the scope as input; and controlling the motion of the scope according to the determined first torque and the second torque.

* * * * *